July 16, 1963 R. V. LINDQUIST Plant Pat. 2,269
ROSE PLANT
Filed July 12, 1962
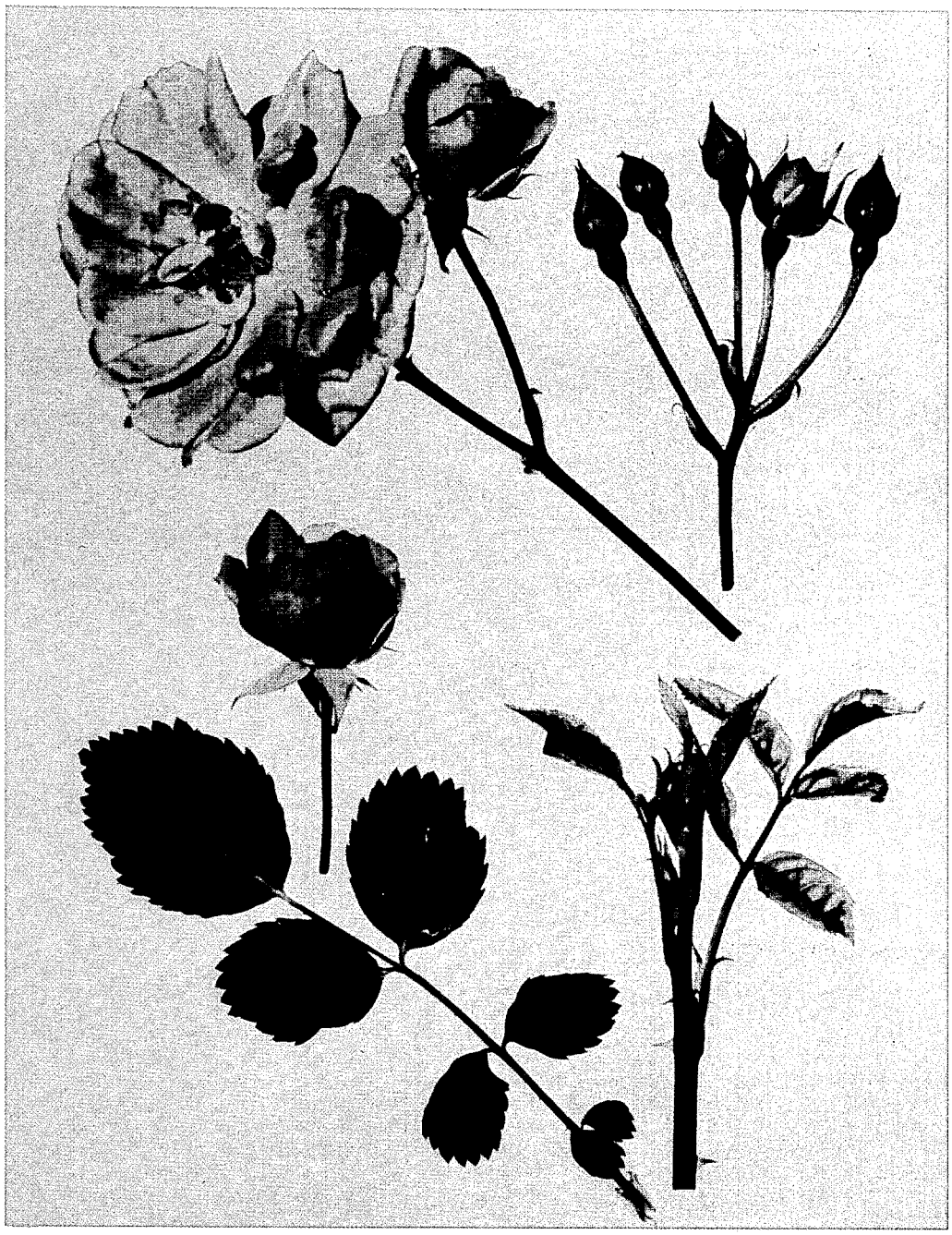
Inventor.
Robert V. Lindquist
By: Robb & Robb
Attorneys.

United States Patent Office

Plant Pat. 2,269
Patented July 16, 1963

2,269
ROSE PLANT

Robert V. Lindquist, Hemet, Calif., assignor to Hemet Wholesale, Hemet, Calif., a partnership Filed July 12, 1962, Ser. No. 209,481
1 Claim. (Plants—27)

The present invention relates to a new and distinct variety of rose plant of the floribunda class, which originated as a sport of the variety known as "Eutin" (unpatented).

The new variety was discovered by me on a plant of the variety "Eutin" which was being grown in the fields of my assignee at Hemet, California, said growing operations being then conducted by me under my personal direction and control. At the time of my discovery aforementioned, my attention was attracted to the sport by the fact that one plant amongst a block of "Eutin" plants bore flowers of a color substantially different from the normal color of the flowers of "Eutin" which ordinarily are Carmine Red in their general color tonality. Upon closer examination of the plant, I found that it had sported, and I thereupon took steps to preserve the sport, keep it under observation, and to asexually reproduce the same for the purpose of determining whether the new flower color was transmissible by asexual propagation. My observations of the original sport, together with the asexual reproductions thereof as performed by me by budding at Hemet, California, fully confirm the new flower characteristics of the sport which may be described as Fuchsine Pink in general color tonality, and conclusively established that the flower color comes true to form and is transmissible through succeeding propagations.

Except for the difference in the color of the flowers, as noted in the foregoing, the new sport is substantially identical with its parent variety "Eutin" which is well known in commerce but is not patented. Accordingly, a detailed description of the new variety will be given hereinafter.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated:

Type: Hardy; bush; for cut flowers and for garden decoration.
Class: Floribunda.
Parentage: Sport of "Eutin."
Propagation: Holds its distinguishing characteristics through succeeding propagations by budding.

*Flower*

Locality where grown and observed: Hemet, California.
Flowers borne: Usually several to stem; in irregular clusters; on strong stems of a length ranging from medium to long.
Quantity of bloom: Free, outdoors.
Continuity: Nearly continuous during growing season.
Fragrance: None.
Bud:

*Peduncle.*—Short; from slender to average caliper; erect; moderately smooth; with some gland-tipped cilia and few hairs. Color—near Oil Green, Plate V (Ridgway).

*Before calyx breaks.*—Size—small. Form—medium length; pointed; globular; with a conspicuous neck; with foliaceous appendages; with tomentum and gland-tipped cilia on the surface of the bud; usually without bristle-like foliaceous parts extending beyond the tip of the bud.

*As calyx breaks.*—Color—near Magenta Rose, Plate 027, page 113 (Wilson).

*Sepals.*—Inner surface—with fine wooly tomentum. Margins—with gland-tipped cilia and hairs.

*As first petals open.*—Size—small. Form—medium length; globular. Color: Outside—near Magenta Rose, Plate 027, page 113 (Wilson), with White, Plate LIII (Ridgway) at base; inside—near Magenta, Plate 27, page 27 (Wilson), with White, Plate LIII (Ridgway) at base.

*Opening.*—Opens up well.

Bloom:

*Size (when fully open).*—Small; from 1½ inches to 2 inches.

*Petalage.*—Double; from 25 to 35 petals, plus 5 to 10 petaloids; arranged irregularly.

*Form.*—Globular at first, but becoming cupped; petals being at first somewhat loosely cupped, with tips rolled outward, but later becoming loosely rolled outward at maturity.

Petals:

*Texture.*—Medium thickness; moderately soft. Inside—slightly satiny. Outside—slightly satiny.

*Shape.*—Outside—round; usually with one notch. Intermediate—round; with one notch. Inside—near oval; apex rounded; with one notch.

This description of a newly opened flower was made from a rose grown outdoors during the month of June at Hemet, California:

*Color.*—Outer petal: outside surface—near Magenta Rose, Plate 027, page 113 (Wilson), with White, Plate LIII (Ridgway) at base; inside surface—near Tyrian Purple, Plate 727, page 159 (Wilson), with White, Plate LIII (Ridgway) at base. Intermediate petal: outside surface—near Magenta Rose, Plate 027, page 113 (Wilson), with White, Plate LIII (Ridgway) at base; inside surface—near Tyrian Purple, Plate 727, page 159 (Wilson), with White, Plate LIII (Ridgway) at base. Inner petal: outside surface—near Magenta Rose, Plate 027, page 113 (Wilson), with White, Plate LIII (Ridgway) at base; inside surface—near Tyrian Purple, Plate 727, page 159 (Wilson), with near White, Plate LIII (Ridgway) at base.

This description was made from a rose that was open for three days outdoors during the month of June at Hemet, California:

*Color.*—Outer petal: outside surface—near Fuchsine Pink, Plate 627/2, page 78 (Wilson), with White, Plate LIII (Ridgway) at base; inside surface—near Fuchsine Pink, Plate 627, page 78 (Wilson), with White, Plate LIII (Ridgway) at base. Inner petal: outside surface—near Fuchsine Pink, Plate 627/1, page 78 (Wilson), with near White, Plate LIII (Ridgway) at base; inside surface—near Fuchsine Pink, Plate 627, page 78 (Wilson), with near White, Plate LIII (Ridgway) at base.

*General color effect.*—Newly opened flower—Fuchsine Pink, Plate 627, page 78 (Wilson). 3-days open — Fuchsine Pink, Plate 627/2, page 78 (Wilson).

*Behavior.*—Drop off cleanly.

*Flower longevity.*—On bush in garden—4 or 5 days in June. Cut roses grown outdoors and kept at living-room temperatures—3 or 4 days in June.

*Reproductive Organs*

Stamens: Average number; arranged irregularly about pistils; a few mixed with petaloids.

Filaments: From short to medium length; most with anthers.

Anthers: Small; all open approximately at once. Color: upper side—near Antimony Yellow, Plate XV (Ridgway); under side—near Warm Buff, Plate XV (Ridgway).

Pollen: Sparse. Color—near Antimony Yellow, Plate XV (Ridgway).

Pistils: Few; approximately 20 in number.

Styles: Uneven; short; thin; somewhat bunched.

Stigma: Color—Pale Greenish Yellow, Plate V (Ridgway).

Ovaries: Usually all enclosed in calyx.

Hips: Does not set hips in south California area.

Sepals: Falling soon; short; spear-shaped; recurved. Color: inside—near Water Green, Plate XLI (Ridgway); outside—near Lettuce Green, Plate V (Ridgway).

Seeds: None.

*Plant*

Foliage:

*Leaves.*—Compound of usually 5 to 7 leaflets; normal quantity; large size; moderately heavy; somewhat leathery and glossy.

*Leaflets.*—Shape—oval, with apex acute. Base—round. Margin—irregularly serrate.

*Color.*—Mature: upper surface—near Deep Dull Yellow-Green (2), Plate XXXII (Ridgway); under surface—near Light Bice Green, Plate XVII (Ridgway). Young: upper surface—near Biscay Green, Plate XVII (Ridgway), with light shadings of Corinthian Purple, Plate XXXVIII (Ridgway); under surface—near Biscay Green, Plate XVII (Ridgway), with shades of Corinthian Purple, Plate XXXVIII (Ridgway).

*Rachis (the supporting stem of the compound leaf).*—Average size. Upper side—grooved; with some stipitate glands on edges. Under side—moderately prickly; with stipitate glands.

*Stipules.*—Medium length; medium width; with moderately short points turning out at an angle of more than 45°.

*Disease resistance.*—Mildly subject to mildew, as determined by comparison with other varieties grown under comparable cultural conditions at Hemet, California.

Growth:

*Habit.*—Bushy; somewhat spreading; moderately branched.

*Growth.*—Very vigorous.

*Canes.*—Medium caliper.

*Main stems.*—Color—near Oil Green, Plate V (Ridgway). Large prickles—few; medium length; almost straight but hooked slightly downward; with base of medium length; color—near Sepia Brown, Plate XXIX (Ridgway). Small prickles—few; color—near Saccardo's Umber, Plate XXIX (Ridgway). Hairs—none.

*Branches.*—Color—near Calla Green, Plate V (Ridgway). Large prickles—very few; medium length; almost straight; with narrow base of medium length; color—Tawny Olive, Plate XXIX (Ridgway). Small prickles—none. Hairs—none.

*New shoots.*—Color—near Yellowish Oil Green, Plate V (Ridgway), with shadings of Madder Brown, Plate XIII (Ridgway). Large prickles—few; medium length; almost straight, but hooked slightly downward; with narrow base of medium length; color—near Cinnamon Buff, Plate XXIX (Ridgway). Small prickles—none. Hairs—none.

I claim:

A new and distinct variety of rose plant of the floribunda class, substantially as herein shown and described, characterized particularly as to novelty by its general similarity to its parent variety "Eutin" (unpatented), but being essentially distinguished therefrom by the Fuchsine Pink general color tonality of its flowers.

No references cited.